United States Patent [19]

McIlroy et al.

[11] Patent Number: 6,093,530
[45] Date of Patent: *Jul. 25, 2000

[54] NON-CALCIFIC BIOMATERIAL BY GLUTARALDEHYDE FOLLOWED BY OXIDATIVE FIXATION

[75] Inventors: Brian K. McIlroy, Georgetown; Mark A. Moore, Austin; Richard E. Phillips, San Marcos, all of Tex.

[73] Assignee: Sulzer Carbomedics Inc., Austin, Tex.

[*] Notice: This patent issued on a continued prosecution application filed under 37 CFR 1.53(d), and is subject to the twenty year patent term provisions of 35 U.S.C. 154(a)(2).

[21] Appl. No.: 09/019,749

[22] Filed: Feb. 6, 1998

[51] Int. Cl.$^7$ .............................. A01N 1/02; A61F 2/00; A61F 2/24
[52] U.S. Cl. ................................ 435/1.1; 424/423; 623/2
[58] Field of Search ............................ 435/1.1; 424/423; 623/2

[56] References Cited

U.S. PATENT DOCUMENTS

| | | | |
|---|---|---|---|
| 4,838,888 | 6/1989 | Nashef | 623/2 |
| 5,147,514 | 9/1992 | Mechanic | 204/157.68 |
| 5,332,475 | 7/1994 | Mechanic | 204/157.68 |
| 5,447,536 | 9/1995 | Girardot et al. | 8/94.11 |
| 5,476,516 | 12/1995 | Seifter et al. | 8/94.11 |
| 5,645,587 | 7/1997 | Chanda et al. | 623/11 |
| 5,697,972 | 12/1997 | Kim et al. | 623/2 |

OTHER PUBLICATIONS

Chvapil et al., "Effect of Collagen Crosslinking on the Rate of Resorption of Implanted Collagen Tubing in Rabbits", J. Biomed. Mater. Res. 11 : 297–314 (1977).
Woodruff, F.A., Ph.D., "Use of Glutaraldehyde and Formaldehyde to Process Tissue Heart Valve", J. Bioeng., vol. 2, pp. 1–9, 1978.
Schoen, F.J., et al., "Cuspal Components in Bioprosthetic Valve Calcification:Education and Modification", Surg. for Heart Valve Disease, pp. 679–685, 1989.
Bernacca, G.M., et al. "Chemical Modification of Bovine Pericardium and Its Effect on Calcification in the Ratsubdermal Model,", Biomaterials, vol. 13, No. 6, pp. 345–352, 1992.
Chanda, J., M.D., "Prevention of Calcification of Heart Valve Bioprostheses; an Experimental Study in Rat", Ann. Thorac. Surg., pp. S339–S342, 1995.
Vesely, I., Ph.D., "The Hybrid Xenograft/Autograft Bioprosthetic Heart Valve:Invivo Evaluation of Tissue Extraction", Ann. Thorac.Surg., pp. S359–S364, 1995.
Okoshi, T., et al., "A New Bioprosthetic Cardiac Valve with Reduced Calcification", ASAIO Trans. pp. M411–M414, 1990.

Oster, G., et al., "Dye Sensitized Photooxidation", J. Am. Chem. Soc., vol. 81, pp. 5095–5099, 1959.
Marcel E. Nimni, The Journal of Biological Chemistry, "A Defect in the Intramolecular and Intermolecular Cross–Linking of Collagen Caused by Penicillamine", Jun. 12, 1967, vol. 243, No. 7, Issue of Apr. 10, pp. 1457–1466.
Carpenter et al., Journal of Thoracic and Cardiovascular Surgery, "Biological Factors Affecting Long–Term Results of Valvular Heterografts", Oct. 1969, vol. 58, No. 4, pp. 467–483.
M.E. Nimni et al., Journal of Biomedical Materials Research, "Chemically Modified Collagen: A Natural Biomaterial for Tissue Replacement", 1987, vol. 21, pp. 741–771.
Levy et al., Circulation "Inhibition by Diphosphonate Compounds of Calcification of Porcine Bioprosthetic Heart Valve Cusps Implanted Subcutaneously in Rats", Feb. 1985, vol. 71, No. 2, pp. 349–356.
Webb et al., Trans. AM. Soc. Artif. Inter. Organs, "Al+++ Preincubation Inhibits Calcification of Bioprosthetic Heart Valve Tissue in the Rat Subdermal Model,", 1988, vol. XXXIV, pp. 855–859.
Matthew Baldwin et al., The 17th Annual Meeting of the Society for Biomaterials, "Fe3+Pretreatment Provides Sustained Inhibition of Bioprosthetic Heart Valve Calcification", May 1991, p. 61.
Mark A. Moore, et al., Journal of Biomedical Materials Research, "Stabilization of Pericardial Tissue by Dye–Mediated Photooxidation", 1994, vol. 28, pp. 611–618.
Hengchu Cao et al., 21st Annual Meeting of the Society for Biomaterials, "Characterization of Mechanical Properties of Photooxidation Modified Bovine Pericardium", 1995, p. 82.

*Primary Examiner*—Sandra Saucier
*Attorney, Agent, or Firm*—Timothy L. Scott; Philip S. Lyren; Kenneth S. Barrow

[57] ABSTRACT

This invention relates to tanning biomaterial to obtain calcification resistant biomaterial with good mechanical properties for bioprosthetic applications. The biomaterial of the invention is obtained by tanning tissue by any method except by oxidation, and then at a later time tanning the tissue by any of the oxidative fixation methods. The process was shown to provide beneficial results with the most frequently used fixation process, which involves fixating tissue with glutaraldehyde. Tissue fixated with glutaraldehyde and then by oxidative fixation has a lower calcification potential than does glutaraldehyde-only tanned tissue and has mechanical properties more similar to glutaraldehyde tanned tissue than to oxidative stabilized tissue. In particular, a process is described where tissue is fixed with glutaraldehyde followed by photoxidation.

10 Claims, No Drawings

NON-CALCIFIC BIOMATERIAL BY GLUTARALDEHYDE FOLLOWED BY OXIDATIVE FIXATION

BACKGROUND OF THE INVENTION

1. Field of the Invention

The present invention relates to a method of preparing biomaterial for prosthetic use that has excellent mechanical properties and high calcification resistance. The method includes the processing of tissues with glutaraldehyde, by standard methods, to fix the tissue. The method then calls for oxidizing the tissue using photosensitive dyes or other means. The resulting tissue has the favorable mechanical properties associated with glutaraldehyde fixation and the resistance to calcification associated with oxidative fixation.

2. Description of the Related Art

Tissue transplantation is a rapidly growing therapeutic field as a result of improvements in surgical procedures, immuno-suppressive treatments, and increased knowledge of the graft-host interaction. Despite major advances, problems associated with tissue transplantation includes inflammation, degradation, calcification, and rejection of the transplanted tissue.

There are several applications for biomaterial tissue transplantation. Heart malfunction due to heart valve disorders can often be treated by surgically implanting a prosthetic valve. Mechanical and bioprosthetic heart valves, made from tanned tissue, are currently in use. Unfortunately, mechanical valves cause severe problems because of the water hammer effect (a transient pressure pulse associated with sudden changes in the velocity of a fluid), poor flexibility, and hemolysis of blood passing through the valve as it nears being fully closed. As a result of the hemodynamic characteristics of mechanical valves, patients are often on life-long anticoagulant therapy.

The limitations of mechanical valves lead to the use of bioprosthetic heart valves (A. Carpentier, J. Thorac. Cardiovasc. Surg., 58: 467, 1969). Tissue derived from porcine aortic valves or bovine pericardium are currently in use. These valves are better than mechanical valves because they have a shape and function similar to the valves they are replacing. In this manner, a centrally orientated blood flow path is maintained, the pressure drop across the valve is lowered, and hemolysis is greatly reduced.

Biomaterial must be stabilized prior to implantation into an animal different from the donor animal. This process of stabilization is known in the art as fixation or tanning. Collagenous biomaterial, usually the major component of a bioprosthesis, can be fixated by treating the material with aldehydes (Nimni et al., J. Biol. Chem. 243:1457–1466, 1968). Later, it was discovered that, of various aldehydes tested, glutaraldehyde best retards degeneration of collagenous tissue (Nimni et al., J. Biomed. Mater. Res. 21:741–771, 1987; Woodroof, E. A., J. Bioeng. 2:1, 1978).

Generally, the fixation process operates by blocking reactive molecules on the surface of and within the donor tissue, thereby rendering it substantially non-antigenic and suitable for implantation as well as crosslinking the collagenous matrix providing stability. Thus, the process of glutaraldehyde-fixation has been and continues to be applied to most varieties of experimental and clinical bioprostheses.

Early experimental and clinical studies of glutaraldehyde-preserved bioprostheses were of bioprosthetic heart valves. Degeneration of collagen and elastin were found to be major factors in the malfunction of bioprosthetic heart valves. Therefore, a method was developed for treating the biomaterial to inhibit inflammatory reactions by host cells while enhancing strength and flexibility, and to prevent the degeneration of collagen and elastin (A. Carpentier, Biological Tissue in Heart Valve Replacement, M. I. Ionescue et al. (Eds.), Butterworth, London, 1972). The method for treating tissues involved washing the tissue in acid, e.g. Hanks solution, and then oxidizing mucopolysaccharide and glycoprotein with metaperiodate to form aldehyde groups, and finally binding and crosslinking the aldehyde groups with amines. The cross-linkages were then stabilized with sodium borohydride.

The data compiled from these early studies demonstrated the excellent biomechanical properties, high resistance to enzymatic degradation, excellent hemodynamic properties and minimal thrombogenicity of the glutaraldehyde-preserved heart valve. However, these bioprostheses may develop failures due to tissue degeneration or, particularly, calcification. Calcification, which causes prosthesis degeneration, is an especially significant disadvantage to the use of tissue-derived prostheses. Indeed, cuspal calcification, i.e. calcification of the bicuspid tissue, accounts for over 60 percent of the failures of cardiac bioprosthetic valve implants, such failures being substantially more frequent in children than in adults.

Calcific deposits in either porcine valves or bovine pericardial valves often nucleate in cell membranes, cell nuclei, and intracellular organelles within 48 hours of transplantation. These deposits increase in size and number over time. The deposits often destroy cells, cleave collagen bundles, and form nodules associated with clinical failure of the tissue (F. J. Schoen et al., in Surgery For Heart Valve Disease: The Proceedings of the 1989 Symposium, E. Bodnar, Ed., 679–85, 1990).

Several methods have been developed to reduce the tendency of the tissue to calcify, but the results are inconclusive. Calcium crystal inhibitors such as phosphonate salts have been put into the tissue (R. J. Levy et al., Circulation, 71: 349, 1985). Detergents such as sodium dodecyl sulfate placed into the tissue inhibit the onset of intrinsic calcium deposition in glutaraldehyde fixed xenograft tissue (D. J. Lentz et al., in Cardiac Biotissue Grafts; Proceedings of the Second International Symposium, L. W. Cohn and V. Galluci, Eds. New York: Yorke Medical Books, 306–19, 1982). Another method of inhibiting calcification is by pretreating the tissue with aluminum ions (C. L. Webb et al., TASAIO, 34: 855,1988), or ferrous ions (M. Baldwin et al., Trans. Soc. Biomat., 14: 61, 1991). Another method of inhibiting calcification is introducing anionic polysaccharides such as chondroitan sulfate (G. M. Bernacca et al., Biomaterials, 13: 345, 1992), or even aspirin to the tissue (U.S. Pat. No. 4,838,888). Yet another method is to covalently bond sulfonated polyethylene oxide to the tissue (U.S. Pat. No. 5,697,972). Moreover, treatment with alpha amino oleic acid may prevent calcification of glutaraldehyde treated bioprosthetic heart valves, but problems with tissue degradation have been reported.

Inactivation of residual glutaraldehyde with an amino compound such as chitosan or glycine--gentamicin prevents calcification in adult rats but not in adolescent rats (J. Chanda, Ann. Thorac. Surg., 60:S339–42, 1994). If the concentration of glutaraldehyde used to treat the tissue does not exceed 0.25%, then subsequent treatment of glutaraldehyde-glycine-gentamican tanned tissue followed by treatment with partially degraded heparin improves resistance to calcification (U.S. Pat. No. 5,645,587). Other methods of treating glutaraldehyde-fixed tissue include soaking the tissue in a polyol such as propylene glycol, 1,3-propanediol, or glycerol (U.S. Pat. No. 5,476,516). The long term stability of these treatments is not known.

It has been found that glutaraldehyde, one of the most popular fixing agents in terms of the mechanical properties of the tissue, enhances susceptibility to calcification. The extent of glutaraldehyde cross-linking is clearly important, although the specific mechanism is not known (C. L. Webb et al., Ann. Thorac. Surg., 60:S359–64,1995). The slow release of residual glutaraldehyde from the prosthesis reinforces host plasma-bound calcium complexes.

Substitutes for glutaraldehyde fixation have been proposed. Efforts have been made to use alternative fixing agents such as carbodiimide in place of glutaraldehyde (T. Okoshi et al., TASAIO, 36; 411, 1990). Cross-linking has been achieved using suberic acid, a di-carboxylic acid, and 1,6-hexane diamine, thereby forming amide linkages (U.S. Pat. No. 5,447,536). Fixing by soaking the tissue in an aqueous solution of photo-oxidative catalyst or compound, followed by exposure to light, thereby fixing the tissue by photo-oxidation, has also been used (M. A. Moore et al., J. Biomed. Mater. Res., 28:611–18, 1994).

Currently, most bioprosthetic tissue is fixed via treatment with glutaraldehyde. Glutaraldehyde treatment provides a tough, durable tissue with mechanical properties often superior to those of alternative methods of fixation. Unfortunately, as described above, calcification of the tissue often results, which leads to failure of the tissue in the patient. The present invention is directed to overcoming or at least reducing the effects of one or more of the problems set forth above.

SUMMARY OF THE INVENTION

This invention relates to the process of fixating biomaterial to obtain calcification resistant biomaterial for bioprosthetic applications. The invention also relates to the biomaterial produced by this process. The biomaterial of the invention is obtained by the combination of fixating the biomaterial at least twice, by two separate methods. The restriction imposed is that oxidation fixation occur after the first method of fixation. The two methods tested, which heretofore have been used only individually and not in combination, are glutaraldehyde fixation and oxidation fixation.

In one embodiment of the present invention biomaterial is fixated with a glutaraldehyde process, the excess glutaraldehyde is then removed, and the tissue is subsequently fixated by dye assisted photooxidation.

Alternative initial fixation processes, such as using alternative fixing agents such as carbodiimide, or using suberic acid, a di-carboxylic acid, and 1,6-hexane diamine, may also be benefited by subsequent fixation of the tissue by the photooxidation process. Alternative subsequent fixation processes include all oxidative stabilization methods, including photooxidation. Photooxidation process and materials described in U.S. Pat. No. 5,332,475 to Mechanic and U.S. Pat. No. 5,147,514 to Mechanic, are incorporated here by reference.

Surprisingly, biomaterial fixated by glutaraldehyde methods, and then later fixated by photooxidation, has the lower calcification potential more similar to photooxidized-only fixated biomaterial, and has mechanical properties more similar to glutaraldehyde-only fixated biomaterial. These favorable results are not observed when biomaterial is first fixated by photooxidation, and then fixated with glutaraldehyde. These favorable results were also not observed in controls where glutaraldehyde fixated tissue was then exposed to either the photosensitive dye or to light, but not both. Surprising results were obtained only when the samples were first fixated with glutaraldehyde, and then fixated by photooxidation.

Variations on these methods and on the materials used, without changing the nature of the process, will be obvious to those skilled in the art. For instance, it may be beneficial to incorporate one or more of the known treatments used to impart calcification resistance to glutaraldehyde fixated tissue either before or after photooxidation. It may also be beneficial to add additional fixation processes.

DETAILED DESCRIPTION OF THE INVENTION

The term "calcification", as used herein, means a deposition of one or more of several calcium compounds, such as calcium phosphate, calcium hydroxyapatite, or calcium carbonate. The presence of these compounds often leads to reduced flexibility and cracking.

As used herein, the term "prosthesis" is meant to include any prosthesis which is derived in whole or part from animal or other organic tissue and which is to be implanted in a mammal. Thus, the term generally includes bioprostheses, such as heart valves and other heart components, vascular replacements or grafts, heart replacements, urinary tract and bladder replacements, bowel and tissue resections in general and the like. However, it will be recognized by those of ordinary skill in the art that the present invention may be of most importance in relation to prostheses for which degeneration and/or calcification after implantation has been a clinical problem.

As used herein the term "biomaterial" is meant to include any material which is derived in whole or part from animal or other organic tissue, and which is to be implanted in a mammal.

As used herein, the terms "fixation," or, interchangeably, "tanning," is meant to be as is generally understood by those of skill in the art, and refers to the process of treating biological tissue in order to stabilize it for implantation in a host individual different from the donor individual. Currently, most bioprosthetic tissue is fixated via treatment with glutaraldehyde, or similar compound.

The process of the present invention provides an efficient and effective method for cross-linking and stabilizing various biomaterial including, but not limited to, collagen, collagen fibrils and collagen matrices. As a general rule, the particular biomaterial utilized as the starting material is determined by the intended use of the product. For instance, if it is desired to build a heart valve from the product of the process of the present invention, the preferred starting biomaterial is a biomaterial having a high collagen content such as the pericardium, for instance, bovine pericardium. If the cross-linked product is to be used as a vascular graft, such starting materials as the aortic arch of rats or other relatively small animals or the carotid artery of pigs, sheep, or cows are used to advantage. To make injectable collagen, finely ground reconstituted bovine skin collagen is used. The material to be cross-linked can also be provided as a tissue sample. Such materials are harvested from the donor animal and immediately immersed in cold buffered saline for storage, with frequent rinses and/or changes with fresh saline, until processed in accordance with the process described herein or solubilized or suspended if finely ground. If the use will be for artery replacement, urinary tract and bladder replacements, bowel and tissue resections in general and the like, the biotissue selected will often have the same function in the donor animal. The choice will depend on the desired properties that the prosthesis should have.

The preferred first fixation process will depend on the intended end use. In many applications, the mechanical properties of a glutaraldehyde tanned sample are desired. In these cases it is preferred to expose the tissue to a glutaraldehyde tanning process. However, other fixation processes are available. The choice of the initial treatment is not important, so long as the first fixation is not by photooxidation. By first fixation, it is meant any treatment, be it a conditioning treatment or tanning treatment, or any number of treatments, that occur before the oxidative fixation.

The particular method of oxidative fixation is not important. Oxidizing agents are used in cooperation with other agents to create localized reduction oxidation reactions. Typical oxidizing agents include (a) a mixture of copper chloride and hydrogen peroxide, (b) a mixture of ascorbate and ferrous chloride, and (c) ferric sulfate. For photooxidation, any of the conventional dyes may be used, and new dyes that have the ability to transfer electrons or in other manner create an oxygen singlet reactive species can be used. The method, and the type of photosensitive dye used, is typically chosen based on the desired degree of activity and the location of activity within the tissue. A preferred method includes exposing the tissue to a high osmolality solution and then exposing the tissue to a high osmolality solution that contains the selected dye. The tissue is later exposed to light while still immersed in the dye solution.

The samples that were selected to be treated by photooxidation only were prepared in the manner described in M. A. Moore, et al., J. Biomed. Matl. Res., 28:611–18, 1994. The tissue samples were immersed in a chilled phosphate-buffered saline solution containing photoactive dye and exposed to a broad-wavelength light source. The dyes are apparently catalysts or precursors which facilitate the formation of an active oxygen singlet. Therefore, the solution should not be deficient in oxygen. Appropriate dyes include, but are not limited to, those listed in Oster, et al., J. Am. Chem. Soc., 81:5095–5096, 1959. Preferred dyes include methylene blue, methylene green, rose bengal, riboflavin, proflavin, fluorescein, rosin, and pyridoxal-5-phosphate. These dyes when activated are believed to cause a transfer of electrons or hydrogen atoms, and thereby oxidize a substrate if oxygen is present. Dependent on the dye and tissue, optimum photooxidation reaction conditions of concentration, time and temperature are used. Tissue specimens are stored at 4° C. in 50% ethanol after treatment.

Fresh bovine pericardium tissue is placed in chilled phosphate-buffered saline at pH 7.4. Fat was removed and sections with heavy vasculature or attached ligaments were discarded. Tissue samples were divided and prepared for treatment. There were about ten individual tissues selected for each treatment, since individual samples show great variability in properties. This tissue was used for all subsequent examples.

EXAMPLE 1

In this example, biomaterial was first fixated using a glutaraldehyde process and then subsequently fixed using a photooxidation process. Glutaraldehyde-tanned samples were prepared using 0.3% glutaraldehyde buffered at pH 7.4. Tissue samples were fixated by three successive immersions in 0.3% glutaraldehyde in phosphate buffered saline (pH 7.3) for 24 hours each at 4° C., room temperature, and 37° C., respectively, with transfer to fresh solution between each immersion. The excess glutaraldehyde was removed by extensive washing with saline or with an aqueous 50% ethanol solution. Tissue specimens were stored at room temperature in 50% ethanol. This is a standard method of tanning tissue with glutaraldehyde.

The glutaraldehyde-tanned-biomaterial was then transferred to a second solution. The second solution contained dissolved methylene blue, was buffered to a pH of about 7. The concentration of the methylene blue was about 0.01% percent by weight.

Following treatment, the mechanical properties of the tanned tissue was tested. Strength was measured as described in Cao, H. and Ryder, J. K., 21st Ann. Trans. Soc. Biomat. 21, 82, 1995. Test specimens were cut using energetic water jet to minimize mechanical damage and maintain precise dimensions of 0.375 inches by 1.2 inches for the uniaxial tension test. Tensile specimens were incorporated into a MTS servohydraulic test machine using friction grips. Uniaxial tensile load was applied to the specimen at a strain rate of 250%/sec. Nine pre-conditioning cycles at a stress level of 4 MPa were applied prior to final pull. The adjusted gage length was used to accommodate creep relaxation. The tensile strength and the failure strain were recorded corresponding to the maximum load. The average of the data is presented as sample "Glutaraldehyde-Photooxidation" in Table 1.

The tanned and photooxidized pericardial tissue samples were subcutaneously implanted into rats and left for 60 days. The tissue were then removed and tested for inflammation. The average of the data is presented as sample "Glutaraldehyde-Photooxidation" in Table 2. The tissues were examined visually for evidence of stiffening that is presumed due to calcification. Visual evidence of stiffening was observed in only one of ten tissues.

Another test for calcification is that of von Kossa staining following histological cross-sectioning. Only one in nine tissues exposed to glutaraldehyde tanning followed by photooxidation was calcified. The quantity of calcification, on a scale where 0 is no calcification and 1 is defined as less than 25% calcified, of these tissue averaged 0.2.

These visual analyses of calcification are subject to some subjectivity. Non-subjective elemental analyses for calcium and phosphorus were performed. The average of the data is shown as sample "Glutaraldehyde-Photooxidation" in Table 3.

EXAMPLE 2

In this example, biomaterial was first fixated using a photooxidation process and then subsequently fixated using a glutaraldehyde process. For these samples, the photooxidation fixation process was performed essentially as described in Example 1. Then, the samples were fixated with glutaraldehyde, following essentially the procedure described in Example 1. The tanned pericardial tissue samples were then subcutaneously implanted into rats and left for 60 days. They were removed, and tested for calcification following the procedures outlined in Example 1. The average of the data is presented as sample "Photooxidation-Glutaraldehyde" in Tables 2 and 3. Performing the two fixation processes in this order produced an inferior product.

COMPARATIVE EXAMPLES 3 to 7

There were a total of five sets of comparative tests. In the third comparative example, the samples were not tanned.

These samples were given the same battery of mechanical and calcification tests that were outlined in Example 1. The average of the data is presented in Tables 1, 2, and 3 under the sample called "Fresh".

In the fourth comparative example, the samples were tanned using the glutaraldehyde method described in Example 1. No subsequent tanning treatment was performed. These samples were given the same battery of mechanical and calcification tests that were outlined in Example 1. The average of the data is presented in Tables 1, 2, and 3 under the sample called "Glutaraldehyde".

In the fifth comparative example, the samples were tanned using the photooxidation method described in Example 1. No subsequent tanning treatment was performed. These samples were given the same battery of mechanical and calcification tests that were outlined in Example 1. The average of the data is presented in Tables 1, 2, and 3 under the sample called "Photooxidation".

In the sixth comparative example, the samples were tanned using the glutaraldehyde method described in Example 1. The procedures for subsequently tanning the tissue by photooxidation described in Example 1 were then carried out, except the photoactive dye was not in the second solution described in Example 1. These samples were given the same battery of calcification tests that were outlined in Example 1. The average of the data is presented in Tables 2 and 3 under the sample called "Glutaraldehyde-Light".

In the seventh comparative example, the samples were tanned using the glutaraldehyde method described in Example 1. The procedures for subsequently tanning the tissue by photooxidation described in Example 1 were then carried out, except the samples were not exposed to the light source described in Example 1. These samples were given the same battery of calcification tests that were outlined in Example 1. The average of the data is presented in Tables 2 and 3 under the sample called "Glutaraldehyde-Dye".

Table 1 contains the results of mechanical properties tests performed on samples treated using the embodiment of the invention described in Example 1 as well as the results of mechanical properties tests performed on three control groups. The treatment of biomaterial by (1) the glutaraldehyde process alone, and (2) the glutaraldehyde process followed by the photooxidation process yielded material with strength near that of fresh tissue. The results of strain tests on tissues tanned with glutaraldehyde and those tanned with glutaraldehyde followed by photooxidation are similar.

TABLE 1

Mechanical Strength of Tanned Bovine Pericardium Tissues

| TEST SAMPLE | Mechanical Analysis* | |
| --- | --- | --- |
| | Strength (Mpa) | Strain |
| Fresh | 8.1 ± 2.3 | 54.0 ± 11.8 |
| Photooxidation | 11.7 ± 2.9 | 51.5 ± 5.8 |
| Glutaraldehyde | 8.5 ± 2.2 | 49.0 ± 7.3 |
| Glutaraldehyde - Photooxidation | 7.7 ± 1.5 | 49.8 ± 6.0 |
| Glutaraldehyde - Light | na | na |
| Glutaraldehyde - Dye | na | na |
| Photooxidation - Glutaraldehyde | na | na |

*Using methods described in Cao, H. and Ryder, J. K., 21st Ann. Trans. Soc. Biomat. 21, 82, 1995.

Tissue samples were subcutaneously implanted into rats and left for 60 days. The tissue were then removed and tested. The visual testing is summarized in Table 2. The untanned (Fresh) tissue showed substantial inflammation, which averaged 2.3 on a scale of zero to four. Those tissues tanned only with glutaraldehyde, and those tissues tanned by photooxidation followed by glutaraldehyde, showed some inflammation. Those tissues tanned by photooxidation only, and those tissues tanned by glutaraldehyde followed by photooxidation, exhibited the smallest amount of inflammation. This shows one reason why tanning with glutaraldehyde and a subsequent tanning by photooxidation is one embodiment of the invention. Treatment by glutaraldehyde followed by photooxidation yields tissue that is less antigenic than is material tanned by glutaraldehyde alone.

TABLE 2

Rat Subcutaneous Explant Analysis For Calcification 60 day Rat Subcutaneous Implant

| TEST SAMPLE | Inflammation* | Visual Calc.** | CALC. HISTOLOGY | |
| --- | --- | --- | --- | --- |
| | | | #/total*** | Ave. Calc.**** |
| Fresh | 2.3 | 0/7 | 0/7 | 0 |
| Photooxidized | 1 | 0/10 | 0/10 | 0 |
| Glutaraldehyde | 1.3 | 3/10 | 5/9 | 1.8 |
| Glutaraldehyde - Photooxidized | 1 | 1/10 | 1/9 | 0.2 |
| Glutaraldehyde - Light | 1 | 2/10 | 2/8 | 0.8 |
| Glutaraldehyde - Dye | 1 | 2/10 | 3/9 | 1.1 |
| Photooxidized - Glutaraldehyde | 1.4 | 4/10 | 4/10 | 1.0 |

*Inflammation is a measure of cellular inflammation on a scale of 0 (no inflammation) to 4.
**Visual Calc. is visually apparent stiffening of explanted tissue; # stiffened/# explants.
***Calc. Histology; #/total is # calcified/# explants determined by von Kossa staining.
****Ave. Calc. is a measure of the severity of calcification, averaged for all explants, where scale ranges from 0 (no calcification) to 1 (scattered mineral deposits) to 2 (less than 25% calcified).

The tissues were examined visually for evidence of stiffening that is presumed due to calcification. The stiffening was observed in four out of ten tissues that were tanned by photooxidation followed by glutaraldehyde. The stiffening was observed in three out of ten tissues tanned by glutaraldehyde only. Visual evidence of stiffening was observed in only one of ten tissues tanned by glutaraldehyde followed by photooxidation, and in none of the ten tissues tanned by photooxidation only. The effects of calcification, i.e., stiffening, are reduced if the final tanning process is a photooxidation process.

Another test for calcification is that of von Kossa staining following histological cross-sectioning. Using this test, fully five of the 9 tissues treated by glutaraldehyde alone examined showed evidence of calcification. The quantity of calcification, on a scale where 0 is no calcification and 1 is defined as less than 25% calcified 2.3 defined as 26–50% calcified, of these tissue averaged 1.8. The tissues exposed to photooxidation followed by glutaraldehyde also did poorly. Four of ten samples were calcified, though the degree of calcification averaged only a 1.0 on the scale previously defined. By contrast, only one in nine tissues exposed to glutaraldehyde tanning followed by photooxidation was calcified. And the degree of calcification was slight, averaging 0.2 on the scale. Controls show that it is the photooxidation itself that is responsible for this increased resistance to calcification. Exposure to light only, or to the photosensitive dyes only, does not impart resistance to calcification.

These visual analyses of calcification are subject to some subjectivity. These visual analyses are also directly supported by non-subjective elemental analyses which are shown in Table 3.

Of the tanned tissue, photooxidation only clearly gives the lowest degree of calcification in all tanned tissues tested. However, there are instances where the mechanical properties of a glutaraldehyde-tanned prosthetic device would be preferred. The tissues that were tanned by glutaraldehyde methods followed by photooxidation showed the next lowest average calcium content. Tissues tanned by glutaraldehyde methods only, and tissues tanned by photooxidation followed by glutaraldehyde methods, showed much higher average calcium concentrations and much higher calcium to phosphorus ratios indicative of biological calcification. A calcium to phosphorus ratio of 1.7 is indicative of natural bone or calcification. As the degree of calcification increases, the ratio of calcium to phosphorus should approach 1.7.

TABLE 3

Elemental Analysis of Implanted Bovine Pericardial Tissue

| TEST SAMPLE | 60 Day Rat Subcutaneous Implant ELEMENTAL CONTENT | | | |
|---|---|---|---|---|
| | Calcium ug/mg | Phosphorus ug/mg | #/total | Ca/P |
| Fresh | 0.3 ± 0.1 | 1.4 ± 0.4 | 0/7 | 0.15 |
| Photooxidation | 0.4 ± 0.1 | 0.9 ± 0.3 | 0/10 | 0.31 |
| Glutaraldehyde | 20.5 ± 28.4 | 9.6 ± 11.8 | 5/9 | 1.65 |
| Glutaraldehyde - Photooxidation | 4.8 ± 9.5 | 3.0 ± 4.3 | 2/9 | 1.26 |
| Glutaraldehyde - Light | 14.3 ± 19.3 | 7.6 ± 9.2 | 4/8 | 1.44 |
| Glutaraldehyde - Dye | 21.1 ± 40.0 | 10.2 ± 17.9 | 3/9 | 1.60 |
| Photooxidation - Glutaraldehyde | 14.1 ± 24.3 | 7.8 ± 11.0 | 6/10 | 1.40 |

This data clearly shows that by treating tissue via a standard glutaraldehyde method, and then treating the tissue by photooxidation, that the mechanical properties are more like the desired glutaraldehyde-only tanned tissues, while the calcification potential is more like the favorable photooxidation-only tanned tissues.

REFERENCES

The following references, to the extent that they provide exemplary procedural or other details supplementary to those set forth herein, are specifically incorporated herein by reference. The reference Moore, et al. J. Biomed. Matl. Res., 28:611–18, 1994 provides details on fixation by photooxidation. The reference U.S. Pat. No. 5,332,475 to Mechanic provides details on fixation by photooxidation. The reference U.S. Pat. No. 5,147,514 to Mechanic provides details on fixation by photooxidation.

What is claimed is:

1. The process of producing calcification retardant biomaterial suitable for use in a bioprosthesis, said biomaterial comprising a biological tissue, said process comprising:

(1) fixating biomaterial by a glutaraldehyde fixation process; and (2) subsequently fixating the biomaterial by an oxidative process which comprises a photooxidation process.

2. The process of claim 1 wherein the fixation process comprises exposing the biomaterial to glutaraldehyde in buffered saline solution.

3. The process of claim 1 wherein the fixation process comprises exposing the biomaterial to glutaraldehyde in phosphate buffered saline solution for about 12 to 36 hours at a temperature from about 10 to 100° C., followed by exposing the biomaterial to glutaraldehyde in phosphate buffered saline solution for about 12 to 36 hours at a temperature from about 15° to 30° C., followed by exposing the biomaterial to glutaraldehyde in phosphate buffered saline solution for about 12 to 36 hours at a temperature from about 30° to 44° C.

4. The process of claim 1 wherein the fixation process comprises exposing the biomaterial to glutaraldehyde in buffered saline solution, and then at a later time the photooxidation process comprises exposing the biomaterial to a solution containing a photosensitive dye, and then exposing the biomaterial in the solution to light in quantities sufficient to cause crosslinking of the tissue.

5. The process of claim 1 wherein the fixation process comprises exposing the biomaterial to glutaraldehyde in buffered saline solution, and the photooxidation process comprises exposing the biomaterial to a solution comprising dissolved oxygen and one or more of a compound selected from methylene blue, methylene green, rose bengal, riboflavin, proflavin, fluorescein, rosin, and pyridoxal-5-phosphate, and then exposing the biomaterial in the solution to light in quantities sufficient to cause crosslinking of the biomaterial.

6. The process of claim 1 wherein the fixation process comprises exposing the biomaterial to glutaraldehyde in phosphate buffered saline solution for about 12 to 36 hours at a temperature from about 1° to 10° C., followed by exposing the biomaterial to glutaraldehyde in phosphate buffered saline solution for about 12 to 36 hours at a temperature from about 15° to 30° C., followed by exposing the biomaterial to glutaraldehyde in phosphate buffered saline solution for about 12 to 36 hours at a temperature from about 30° to 44° C., and the photooxidation process comprises exposing the biomaterial to a solution comprising dissolved oxygen and one or more of a compound selected from methylene blue, methylene green, rose bengal, riboflavin, proflavin, fluorescein, rosin, and pyridoxal-5-phosphate, and then exposing the tissue in the solution to light in quantities sufficient to cause crosslinking of the tissue.

7. The process of claim 1 wherein the fixation process comprises exposing the biomaterial to glutaraldehyde in buffered saline solution, and the photooxidation process comprises exposing the biomaterial to a solution comprising dissolved oxygen and riboflavin, and then exposing the biomaterial in the solution to light in quantities sufficient to cause crosslinking of the biomaterial.

8. The process of claim 1 wherein the fixation process comprises exposing the biomaterial to glutaraldehyde in phosphate buffered saline solution for about 12 to 36 hours at a temperature from about 1° to 10° C., followed by exposing the tissue to glutaraldehyde in phosphate buffered saline solution for about 12 to 36 hours at a temperature from about 15° to 30° C., followed by exposing the biomaterial to glutaraldehyde in phosphate buffered saline solution for about 12 to 36 hours at a temperature from about 30° to 44° C., and the photooxidation process comprises exposing the biomaterial to a solution comprising dissolved oxygen and riboflavin, and then exposing the biomaterial in the solution to light in quantities sufficient to cause crosslinking of the tissue.

9. The process of claim 1, wherein said calcification retardant biomaterial is stable following implantation in a host.

10. The process of claim 1, wherein said biological tissue is a heart tissue.

* * * * *